United States Patent
Cecchi et al.

(10) Patent No.: US 6,649,627 B1
(45) Date of Patent: Nov. 18, 2003

(54) PHENOXYLPROPANOLAMINES, METHOD FOR THE PRODUCTION THEREOF AND PHARMACEUTICAL COMPOSITIONS CONTAINING THE SAME

(75) Inventors: Roberto Cecchi, Lodi (IT); Tiziano Croci, Milan (IT); Umberto Guzzi, Milan (IT); Eric Marsault, Sherbrooke (CA)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/719,640

(22) PCT Filed: Jun. 10, 1999

(86) PCT No.: PCT/FR99/01370

§ 371 (c)(1),
(2), (4) Date: Mar. 26, 2001

(87) PCT Pub. No.: WO99/65895

PCT Pub. Date: Dec. 23, 1999

(30) Foreign Application Priority Data

Jun. 18, 1998 (FR) .............................................. 98 07660

(51) Int. Cl.$^7$ ..................... A61K 31/445; C07D 213/02
(52) U.S. Cl. ....................................... 514/318; 546/194
(58) Field of Search ............................ 546/194; 514/318

(56) References Cited

U.S. PATENT DOCUMENTS

| | | | | |
|---|---|---|---|---|
| 4,425,362 A | * | 1/1984 | Berthold et al. | 424/322 |
| 5,145,967 A | * | 9/1992 | Lin et al. | 546/208 |
| 5,541,195 A | * | 7/1996 | Schilling et al. | 514/311 |
| 5,767,116 A | * | 6/1998 | Kerrigan et al. | 514/212 |

FOREIGN PATENT DOCUMENTS

| EP | 00502072 | 5/1982 |
|---|---|---|
| FR | 2567885 | 1/1986 |
| WO | WO 95/07274 | 3/1995 |

\* cited by examiner

Primary Examiner—Alan L. Rotman
Assistant Examiner—Raymond Covington
(74) Attorney, Agent, or Firm—Michael D. Alexander

(57) ABSTRACT

The invention concerns compounds of formula (Ia)

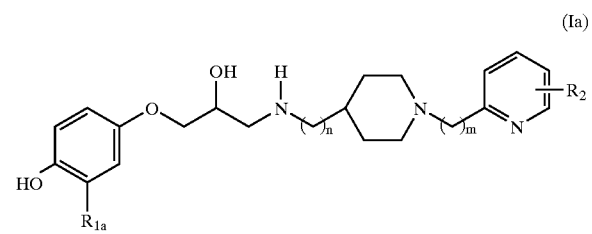

wherein $R_{1a}$ represents hydrogen, an —S(O)$_z$—(C$_1$–C$_4$)Alk group, a —CO(C$_1$–C$_4$)Alk group, an —NHSO$_2$—(C$_1$–C$_4$)Alk group, an NCHl (C$_1$–C$_4$) Alk group, a 2-furyl group or a halogen;

$R_2$ represents hydrogen or a (C$_1$–C$_4$)Alk group, a (C$_1$–C$_4$) alkoxyl group, a halogen, —COOH, —COO(C$_1$–C$_4$) Alk, —CN, —CONR$_3$R$_4$, —NO$_2$, —SO$_2$NH$_2$, —NHSO$_2$(C$_1$–C$_4$)Alk;

m and n are independently 0, 1 or 2;

$R_3$ and $R_4$ independently represent hydrogen or a (C$_1$–C$_4$) Alk group;

Z is 1 or 2 and their salts or solvates, the pharmaceutical compositions that contain them, the process for their preparation, and intermediate synthesis products.

39 Claims, No Drawings

PHENOXYLPROPANOLAMINES, METHOD FOR THE PRODUCTION THEREOF AND PHARMACEUTICAL COMPOSITIONS CONTAINING THE SAME

This invention concerns new phenoxypropanolamines, the pharmaceutical compositions that contain them, a process for their preparation and intermediate products in this process.

BE 902897 describes aryloxypropanolamines with a 4-piperidininyl-1group substituted on the amine, these compounds having beta-blocking and alpha-blocking activity.

J. Org. Chem., 1988, 63:889:894 describes other aryloxypropanolamines having a 4-piperidininyl-1 group substituted on the amine.

It has now been found that phenoxypropanolamines having a 1-(pyrid-2-yl)-piperidine-4-yl radical on the amine have an agonistic activity with regard to adrenergic $\beta_3$ receptors.

Accordingly the present invention concerns, in one of its aspects, phenoxypropanolamines of formula (Ia)

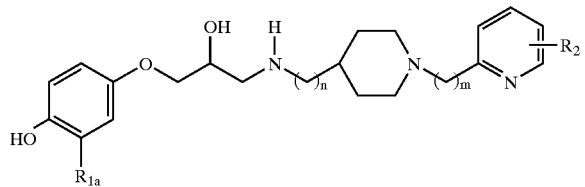

$R_{1a}$ represents hydrogen, an —S(O)$_z$ —(C$_1$–C$_4$)Alk group, a —CO(C$_1$–C$_4$)Alk group, an —NHSO$_2$ —(C$_1$–C$_4$)Alk group, an NHCO(C$_1$–C$_4$)Alk group, a 2-furyl group or a halogen;

$R_2$ represents hydrogen, or a (C$_1$–C$_4$)Alk group, a (C$_1$–C$_4$)alkoxyl group, a halogen, —COOH, —COO (—(C$_1$–C$_4$)Alk, —CN—CONR$_3$R$_4$—NO$_2$, —SO$_2$NH$_2$, —NHSO$_2$ (C$_1$–C$_4$)Alk;

m and n are independently 0, 1 or 2;

R$_3$ and R$_4$ independently represent hydrogen or a (C$_1$–C$_4$) Alk group;

Z is 1 or 2;

and their salts or solvates.

According to another of its aspects, the invention concerns compounds of formula (I):

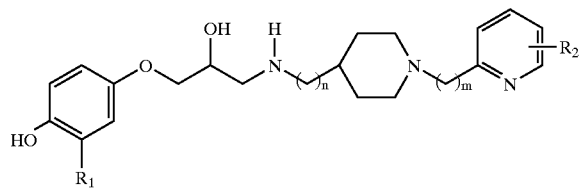

wherein

R$_1$ represents hydrogen, an —S(O),—(C$_1$–C$_4$)Alk group, a —CO(C$_1$–C$_4$)Alk group or an —NHSO$_2$—(C$_1$–C$_4$) Alk group;

R$_2$ represents hydrogen or a (C$_1$–C$_4$)Alk group, a (C$_1$–C$_4$) alkoxyl group, a halogen, —COOH, —COO(C$_1$–C$_4$) Alk;

m and n are independently 0, 1 or 2;

R$_3$ and R$_4$ independently represent hydrogen or a (C–C$_4$) Alk group;

Z is 1 or 2 and their salts or solvates.

In the present description the term "(C$_1$–C$_4$)Alk" designates a monovalent radical of a saturated hydrocarbon in C$_1$–C$_4$ with a straight or branched chain.

The salts of compounds of formula (I) according to the present invention comprise equally the addition salts with inorganic or organic acids that are pharmaceutically acceptable such as hydrochloride, hydrobromate, sulphate, hydrogen-sulphate, dihydrogenphosphate, citrate, maleate, tartrate, fumarate, gluconate, methane sulphonate, 2-naphthalene sulphonate, and so on, and the addition salts that permit separation or suitable crystallisation of compounds of formula (I), such as the picrate, oxalate or the addition salts with optically active acids, for example the camphor sulphonic acids and the mandelic or substituted mandelic acids.

Moreover, when the compounds of formula (I) and (Ia) possess a free carboxyl group the salts also comprise the salts with inorganic bases, preferably those with alkaline metals such as sodium or potassium, or with organic bases.

The optically pure stereo-isomers, together with the mixtures of isomers of compounds of formula (I) and (Ia), due to asymmetrical carbons or to the sulfinyl group, in the meaning of $R_{1a}$ or $R_1$, in any proportions, form part of the present invention.

Preferred compounds of the present invention comprise the compounds of formula (I) and (Ia) in which the R$_2$ group is at position 5 of the pyridine.

Other preferred compounds comprise the compounds of formula (I) or (la) wherein the R$_2$ group is in position 6 of the pyridine.

Other preferred compounds are those in which the (C$_1$–C$_4$) Alk group is a methyl or ethyl group.

Other preferred compounds are those in which R$_2$ is one of the following: —COOH, —COO(C$_1$–C$_4$)Alk, —CN, —NO$_2$, —CONR$_2$R$_3$, or —NHSO$_2$(C$_1$–C$_4$)Alk.

Other preferred compounds are those in which R$_2$ is a halogen, notably chlorine.

Other preferred compounds are those in which n and m are zero.

The compounds of formula (I) and (Ia) can be prepared by treating a compound of formula (II)

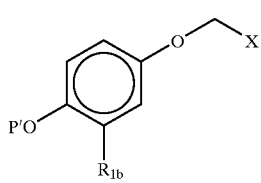

in which R$_1$b is R$_{1a}$ or R$_1$ as indicated above, P' is a protective group and X is a group of formula (a) or (b)

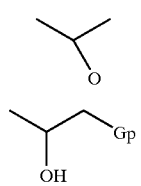

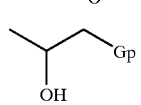

where Gp is an initial group such as tosylate, mesylate or a halogen, with an amine of formula (III).

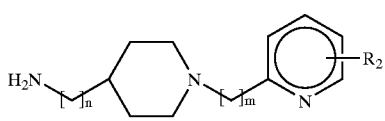

(III)

wherein n, m and $R_2$ are as defined above, with the P' group split off by the usual methods and as appropriate converting the compound of formula (I) or (Ia) obtained into one of these salts.

More particularly, the reaction between the compounds of formulas (I) and (III) is carried out in an organic solvent, for example a lower alcohol such as methanol, ethanol or isopropanol; dimethylsulphoxide; a linear or cyclic ether; an amide such as dimethylformamide or dimethylacetamide; using at least equimolecular quantities of the reagents, with a slight excess of amine as appropriate.

The reaction temperature is between room temperature and the reflux temperature of the chosen solvent.

The protective groups P' can be the usual protective groups for the hydroxyl groups such as for example methoxyethoxymethyl (MEM) or benzyl.

These protective groups are split off using the normal methods for the protective group selected; for example in the case of the benzyl group by hydrogenation in the presence of a catalyst such as Pd/C in a suitable solvent; however in the case of methoxyethoxymethyl (MEM) it is possible to use an acid such as trifluoroacetic acid.

Most of the epoxides in formula (II) are compounds known in the literature or alternatively can be prepared by processes similar to those described in the literature. For example certain epoxides of formula (II) are described in WO 96/04233 and in U.S. Pat. No. 4,396,629.

The pure isomers of the compounds of formula (II) in which X is a group (a) and $R_{ab}$ represents the $SOCH_3$ group, resolved to the asymmetrical carbon, are new, having been obtained for the first time as pure stereo-isomers free of other stereo-isomers or impurities.

Certain epoxides of formula (II) are new and constitute another object of the present invention.

More particularly, these are compounds of formula (II'):

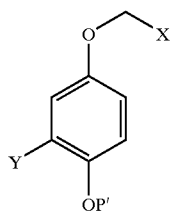

(II')

wherein P' is as defined in formula (II), X is a group (a) as defined above and Y represents an atom of bromine or a 2-furyl group, their optically active isomers and their salts. They are prepared as described in examples 44 and 47.

The amines of formula (III) can be prepared by reacting appropriate pyridines of formula (IV)

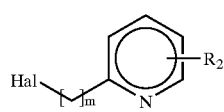

(IV)

where Hal represents a halogen and $R_2$ and m are as defined above, with a piperidine of formula (V) below

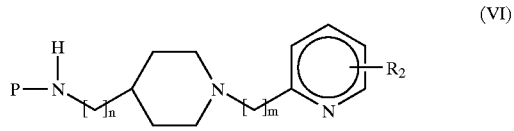

(V)

where n is as defined above and P represents a protective group, in an organic solvent in the presence of a base, followed by splitting off the P group from the compounds of formula (VI) obtained.

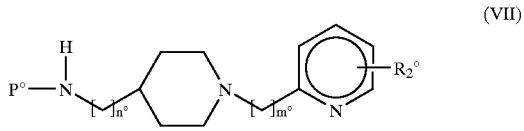

(VI)

As a reaction solvent for example, it is possible to use dimethylformamide, pyridine, dimethylsulphoxide, a linear or cyclic ether or a chlorinated solvent such as dichloromethane.

As a base for example one can use an alkaline hydroxide, an alkaline carbonate such as potassium carbonate or a tertiary amine such as triethylamine.

The above condensation reaction takes a few hours, normally between 2 and 12 hours.

The reaction temperature is between room temperature and the reflux temperature for the chosen solvent.

As protective groups P it is possible to use the usual protective groups for amines, for example ter-butoxycarbonyl, acetyl, or carbobenzyloxy.

These protective groups are split off using the normal methods described for the selected protective group; for example in the case of ter-butoxycarbonyl, splitting off is normally done by acid hydrolysis.

Certain intermediate amines of a formula (III) and (VI), grouped together in formula (VII) below

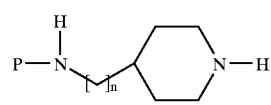

(VII)

where

P° is hydrogen or a protective group;

n° and m° are 0, 1 or 2;

$R°_2$ is a $(C_1-C_4)Alk$; $(C_1-C_4)alkoxyl$, —COOH, —COO$(C_1-C_4)Alk$, —CN, —NO$_2$, —CONR$_3°$R$_4°$, —SO$_2$NH$_2$, or —NHSO$_2(C_1-C_4)Alk$;

$R°_3$ and $R°_4$ are hydrogen or a $(C_1-C_4)Alk$ group; on condition that:

when n° and m° are zero, $R°_2$ is other than methoxyl at position 6 and other than halogen in position 3 or 6 on the pyridine; when n° is 1, m° is 0, $R°_2$ is other than chlorine in position 6 of the pyridine and when n° is 0, m° is 0 or 1, $R°_2$ is other than methyl; and their salts, are new compounds and are a later subject of the present invention.

Particularly preferred compounds of formula (VII) are those in which $R°_2$ is chosen from the groups —COOH, —COO$(C_1-C_4)Alk$, —CN, NO$_2$, —CONR$_3°$R$_4°$, —SO$_2$NH$_2$, and —NHSO$_2(C_1-C_4)Alk$.

Other preferred compounds of formula (VII) are those in which $R°_2$ is at position 5 of the pyridine.

Other preferred compounds of formula (VII) are those in which n° and m° are zero.

Other particularly preferred compounds of formula (VII) are those in which P° is hydrogen.

The compounds of formula (I) have shown very strong affinity for the $\beta_3$ receptors.

The activity of the compounds of the present invention with regard to $\beta_3$ activity has been demonstrated by in vitro tests on the human colon using the method described in EP-B-436435 and in T. Croci et al, Br. J. Pharmacol., 1997, 122: 139P.

It was noted in particular that the compounds of formula (I) and (Ia) are much more active on the isolated colon than on the auricle and the trachea.

These surprising properties of the compounds of formula (I) and (Ia) suggest that they could be used as $\beta_3$ action drugs.

Moreover the compounds of formula (I) and (Ia) are only slightly toxic; in particular their acute toxicity is compatible with their use as drugs for treating diseases where compounds having an affinity for the ###$_3$ receptor are applied. The compounds of formula (I) and (Ia), together with their pharmaceutically acceptable salts, may therefore be indicated for example for the treatment of gastro-intestinal diseases such as irritable bowel syndrome, as modulators of intestinal peristalsis such as the lipolytics, and anti-obesity, anti-diabetic, psychotropic, anti-glaucoma, healing and anti-depressant agents, as an inhibitor of uterine contractions, as tocolytic agents to prevent or delay premature births, and for treating and/or prophylaxis of dysmenorrhoea.

The use of compounds of formula (I) and (Ia) above, and of their pharmaceutically acceptable salts and solvates for preparing the above drugs constitutes a later aspect of the present invention.

For such a purpose, mammals that necessitate such treatment are administered an effective quantity of a compound of formula (I) or (Ia) or of one of its pharmaceutically acceptable salts and solvates.

The compounds of formula (I) and (Ia) above and their pharmaceutically acceptable salts and solvates can be used in daily doses of 0.01 to 20 mg per kilo of body weight of the mammal to be treated, preferably in daily doses of 0.1 to 10 mg/kg. In man, the dose can vary for preference from 0.5 mg to 1500 mg a day, notably from 2.5 to 500 mg according to the age of the patient, the type of treatment (prophylactic or curative) and the gravity of the disease. The compounds of formula (I) and (Ia) are usually administered in dose units of 0.1 to 500 mg, preferably 0.5 to 100 mg of active principle, from 1 to 5 times a day.

The said dose units are preferably formulated in pharmaceutical compounds in which the active principle is mixed with a pharmaceutical excipient.

Thus according to another of its aspects, the present invention concerns pharmaceutical compositions in which the active principle is a compound of formula of (I) or (Ia) above or one of its pharmaceutically acceptable salts and solvates.

In the pharmaceutical compositions of the present invention for oral, sublingual, subcutaneous, intramuscular, intravenous, topical, transdermal or rectal administration, the active ingredients of formula (I) or (Ia) above, and their pharmaceutically acceptable salts and solvates, can be administered in unitary forms mixed with conventional pharmaceutical media, to animals and man, for treating the above-mentioned diseases. The appropriate unitary forms of administration comprise the forms given by mouth such tablets, capsules, powders, granules and oral solutions or suspensions, the sublingual and buccal forms of administration, the subcutaneous, intramuscular or intravenous forms of administration, the local forms of administration and the rectal forms of administration.

When a solid composition is prepared in the form of tablets, the principal active ingredient is mixed with the pharmaceutical vector such as gelatine, starch, lactose, magnesium stearate, talc, gum arabic or similar. The tablets may be coated with saccharose or other suitable materials or they may be processed in such a way that their activity is extended or delayed so that they release a predetermined quantity of active principle on a continuous basis.

A capsule preparation is obtained by mixing the active ingredient with a diluent and pouring the mixture produced into soft or rigid capsules.

A preparation in the form of syrup or tincture can contain the active ingredient together with a sweetener, preferably of the low-calorie variety, methylparaben and propylparaben as antiseptics, together with a flavour agent and an appropriate colour.

Powders and granules that are dispersible in water may contain the active ingredient mixed with dispersion agents or wetting agents, or suspension agents, such as polyvinylpyrrolidone, and with sweeteners or flavour correctors.

For local administration, the active principle is mixed with an excipient for preparing creams or unguents or it is dissolved in a vector for administration into the eye, for example in the form of eye drops.

For rectal administration, suppositories are used that are prepared with binders that melt at rectal temperature, for example cocoa butter or polyethylene glycols.

For administration into the digestive tract, aqueous suspensions, saline solutions or sterile injectable solutions are used that contain dispersion agents and/or pharmacologically compatible wetting agents, for example propylene glycol or butylene glycol.

The active principle may also be formulated in the form of microcapsules, possibly with one or more vectors or additives.

According to another of its aspects, the present invention concerns a method of treating diseases that are improved by a ###$_3$-agonistic action, which involves administering a compound of formula (I) or (Ia) or one of its pharmaceutically acceptable salts or solvates.

The compounds of formula (I) and (Ia), notably the compounds (I) and (Ia) marked by an isotope, can also be used as laboratory tools in biochemical tests.

The compounds of formula (I) and (Ia) bind to the ###$_3$-adrenergic receptor. These compounds can therefore be used an ordinary binding test, that utilise an organic tissue in which this receptor is particularly abundant, and the quantity of compound (I) or (Ia) displaced by a test compound is measured, in order to evaluate the affinity of the said compound for the bonding sites of this particular receptor.

Another specific object of the present invention is therefore a reagent that can be used in biochemical tests that comprises at least one compound of formula (I) or (Ia) appropriately marked.

The following examples give a better illustration of the invention.

PREPARATION 1

4-ter-Butoxycarbonylamino-piperidine 25 g (0.13 mole) of 4-amino-1-benzylpiperidine, 36.2 ml (0.26 mole) of triethylamine and 31.2 g (0.143 mole) of di-ter-butyl-dicarbonate are mixed at room temperature for 2 hours in 200 ml of dimethylformamide. The mixture is poured into water, extracted with ethyl acetate, washed with water and the product obtained crystallised in 200 ml of isopropyl ether. This produces 33 g of 1-benzyl-4-ter-butoxycarbonylamino-piperidine which is hydrogenated in a mixture of 200 ml of ethanol and 100 ml of tetrahydrofurane in the presence of 3 g of 10% Pd/C. After filtering the catalyst, the named compound is isolated; M. P. 157–160° C.

PREPARATION 2

4-ter-Butoxycarbonylaminomethyl-piperidine

Proceed as for preparation 1, but using 4-aminomethyl-1-benzylamine instead of the 4-amino-1-benzylamine, producing the named compound M. P. 105–107° C.

Example 1

4-ter-Butoxycarbonylamino-1-(5-aminocarbonylpyrid-2-yl)-piperidine

A mixture of 3 g (0.015 mole) of the product of preparation 1, 1.5 g (0.025 mole) of triethylamine and 2.34 g (0.015 mole) of 6-chloronicotinamide is heated to 80° C. for 18 hours in 60 ml of dimethylformamide. After cooling, water is added and the product filtered. This produces 2.8 g of the named compound M. P. 255° C.

Example 2

4-Amino-1-(5-aminocarbonylpyrid-2-yl)-piperidine and its Semi-hydrated Dihydrochloride 1.84 g (0.0057 mole) of the product of example 1 is mixed with 50 ml of ethyl acetate. 50 ml of 3N hydrochloric acid solution in ethyl acetate is added while stirring, and stirring is continued at room temperature for 10 hours. The mixture is filtered and washed with acetone. This produces 1.67 g of the named compound M. P. 290° C.

Example 3

4-ter-Butoxycarbonylamino-1-(5-ethoxycarbonylpyrid-2-yl)-piperidine

A mixture as described in example 1 is reacted but using the ethyl ester of the 6-chloronicotinic acid instead of the 6-chloronicotinamide. After cooling, water is added, the ethyl acetate extracted, the organic phase extracted on sodium sulphate and the solvent evaporated off under reduced pressure. The named compound M. P. 140–142° C. is obtained.

Example 4

4-Amino-1-(5-ethoxycarbonylpyrid-2-yl)-piperidine and its Hydrated Dihydrochloride By proceeding as described in example 2, but using the product of example 3 instead of the product of example 1, the named compound M. P. 148–150° C. is obtained.

Example 5

4-ter-Butoxycarbonylamino-1-(5-nitropyrid-2-yl)-piperidine

By proceeding as described in example 1 but using 2-chloro-5-nitropyridine instead of the 6-chloronicotinamide, the named compound M. P. 220° C. is obtained.

Example 6

4-Amino-1-(5-nitropyrid-2-yl)-piperidine

By proceeding as described in example 2 but using the product of example 5 instead of the product of example 1, the hydrochloric compound M. P. 266–270° C. is obtained. The base is released using a solution of $H_2O/NH_4OH$ and extracted with ethyl acetate. The named compound M. P. 115–117° C. is obtained.

Example 7

4-ter-Butoxycarbonylamino-1-(5-cyanopyrid-2-yl)-piperidine

By proceeding as described in example 1 but using 2-chloro-5-cyanopyridine instead of the 6-chloronicotinamide, the named compound M. P. 192–194° C. is obtained.

Example 8

4-Amino-1-(5-cyanopyrid-2-yl)-piperidine

By proceeding as described in example 2 but using the product of example 7 instead of the product of example 1, and treating the hydrochloric salt obtained with an aqueous solution of $NH_4OH$, the named compound M. P. 68–72° C. is obtained.

Example 9

9a/3-[1-(5-Aminocarbonylpyrid-2 -yl)-4-piperidinylamino]-1-(4g -benzyloxyphenoxy)-2-propanol 1.2 g (0.0054 mole) of the product of example 2 (base) and 1.4 g (0.0054 mole) of 4-benzyloxy-1-(2,3-epoxypropoxy) benzene are mixed in 50 ml of dimethylsulphoxide and heated at 70° C. for 18 hours. This is poured into water, extracted with ethyl acetate, dried, filtered and the solvent evaporated off under reduced pressure. The named compound M. P. 160–162° C. is obtained.

9b/3-[11-(5-Aminocarbonylpyrid-2-yl)4-piperidinylamino]-1-(4-hydroxyphenoxy)-2-propanol 0.77 g of the compound of the previous step is hydrogenated at 40° C. at ambient pressure in 30 ml of THF and 30 ml of ethanol in the presence of 0.1 g of 10% Pd/C for about 6 hours. The catalyst is filtered and evaporated under reduced pressure. The reaction product is purified by flash chromatography, using an 8/2 mixture of methylene chloride and methanol as eluant. The named compound M. P. 192–194° C. is obtained.

Example 10

3-[1-(5-Aminocarbonylpyrid-2-yl)-4-Piperidinylamino]-1-(4-Hydroxyphenoxy)-2-propanol By proceeding as described in example 9 but using the product of example 4 instead of the product of example 2, the named compound M. P. 157–159° C. is obtained.

Example 11

3-[1-(5-Cyanopyrid-2-yl)4-piperidinylamino]-1-(4-hydroxyphenoxy)-2-propanol

By proceeding as described in example 9 but using the product of example 8 instead of the product of example 2, the named compound M. P. 160–162° C. is obtained.

Example 12

3-[1-(5-Nitropyrid-2-yl)-4-piperidinylamino]-1-(4-hydroxyphenoxy)-2-propanol 12a/3-[1-(5-nitropyrid-2-yl)-4-piperidinylamino]-1-4-methoxy-ethoxy-methoxyphenoxy)-2-propanol

A mixture of 1.06 g (0.0048 mole) of the product of example 6 and 1.21 g (0.0048 mole) of 4-(methoxy-ethoxy-methoxy)-1-(2,3-epoxypropoxy)-benzene is heated under reflux for 17 hours in 40 ml of ethanol. The product is filtered and crystallised in 25 ml of absolute ethanol. This produces the named compound M. P. 122–124° C.

12b/3-[1-(5-Nitropyrid-2-yl)-4-piperidinylamino]-1-4-hydroxyphenoxy)-2-propanol

2 ml of $CF_3COOH$ in 5 ml of methylene chloride is added to a solution of 1.2 g (0.0025 mole) of the product of the previous step in 10 ml of methylene chloride. This is stirred at room temperature for 48 hours. The mixture is poured into water, a solution of $H_2O/NH_4OH$ is added until a basic pH is reached, this is extracted with ethyl acetate and the solvent evaporated off under reduced pressure. The substance is purified by flash chromatography (eluant: methylene chloride/methanol=9/1). The named compound M. P. 195–197° C. is obtained.

Example 13

4-ter-Butoxycarbonylamino-1-(4-ethoxycarbonylpyrid-2-yl)-piperidine

By proceeding as described in example 33 but using the ethyl ester of 2-chloro-4-pyridine carboxylic acid instead of the ethyl ester of 6-chloronicotinic acid, the named compound M. P. 105–107° C. is obtained.

Example 14

4-Amino-1-(4-ethoxycarbonylpyrid-2-yl)-piperidine and its Hydrated Dihydrochloride

By proceeding as described in example 2 but using the product of example 13 instead of the product of example 1, the named compound M. P. 222–224° C. is obtained.

Example 15

3-[1-(4-Ethoxycarbonylpyrid-2-yl)-piperidylamino]-1-(4-hydroxyphenoxy)-2-propanol

By proceeding as described in example 9 but using the product of example 14 (base) instead of the product of example 2, the named compound M. P. 115–117° C. is obtained.

Example 16

4-ter-Butoxycarbonylamino-1-(Pyrid-2-ylmethyl)-piperidine

By proceeding as described in example 3 but using 2-chloromethyl pyridine instead of the ethyl ester of 6-chloronicotinic acid, the named compound M. P. 98–100° C. is obtained.

Example 17

4-Amino-1-(pyrid-2-yl-methyl)-piperidine and its Dihydrated Hydrochloride

By proceeding as described in example 2 but using the product of example 16 instead of the product of example 1, the named compound M. P. 270–273° C. is obtained.

Example 18

3-[1-(Pyrid-2-yl-Methyl)4-Piperidinylamino]-1-(4-Hydroxy-Phenoxy)-2-Propanol

By proceeding as described in example 9 but using the product of example 17 (base) instead of the product of example 2, the named compound M. P. 190–192° C. is obtained.

Example 19

4-ter-Butoxycarbonylaminomethyl-1-(5-ethoxycarbonylpyrid-2-yl)-piperidine

By proceeding as described in example 3 but using the product of preparation 2 instead of the product of preparation 1, the named compound M. P. 118–120° C. is obtained.

Example 20

4-Aminomethyl-1-(5-ethoxycarbonylpyrid-2-yl-)-piperidine and its Dihydrochloride

By proceeding as described in example 2 but using the product of example 19 instead of the product of example 1, the named compound M. P. 230–232° C. is obtained.

Example 21

3-[1-(-Ethoxycarbonylpyrid-2-yl)-4-piperidinylmethyl]amino)-1-(4-hydroxyphenoxy)-2-propanol and its Hydrochloride

By proceeding as described in example 9 but using the product of example 20 (base) instead of the product of example 2, the basic compound is obtained. The hydrochloride is prepared using a solution of hydrochloric acid in isopropanol. The named compound M. P. 195° C. is obtained.

Example 22

4-ter-Butoxycarbonylamino-1-(pyrid-2-yl)-piperidine

By proceeding as described in example 3 but using 2-bromopyridine instead of the ethyl ester of 6-chloronicotinic acid, the named compound M. P. 118–120° C. is obtained.

Example 23

4-Amino-1-(pyrid-2-yl)-piperidine and its Hydrochloride

By proceeding as described in example 2 but using the product of example 22, the named compound M. P. 227–230° C. is obtained.

Example 24

3-[1-(Pyrid-2-yl)4-piperidinylamino]-1-(4-hydroxyphenoxy)-2-Propanol and its Hydrated Hydrochloride

By proceeding as described in example 9 but using the product of example 23 (base) instead of the product of example 2, and absolute ethanol instead of dimethylsulphoxide we obtain the basic compound. The hydrochloride is prepared using a solution of hydrochloric acid in isopropanol. The named compound M. P. 137–139° C. is obtained.

Example 25

(2S)-3-[1-(5-Ethoxycarbonylpyrid-2-yl)4-piperidinylamino-1-(4-hydroxy-phenoxy)-2-propanol

25a)(2S)-3-[1-(5-Ethoxycarbonylpyrid-2-yl)-4-piperidinylamino-1-(4-benzyloxy-phenoxy)-2-propanol 0.81 g (0.333 mole) of the product of example 4 is mixed with 0.83 g (0.0033 mole) of (2S)-4-benzyloxy-1-(2,3-epoxypropoxy) benzene in 90 ml of ethanol and heated under reflux for 20 hours. The solvent is evaporated off and ethyl ether is added. The reaction product is filtered and purified by chromatography, eluting with a 95/5 mixture of methylene chloride and methanol. The named compound melting at 105–107° C. is obtained; [$\alpha_D$]=−5.12° (C=1% CHCl$_3$).

25b)(2S)-3-[1-(5-Ethoxycarbonylpyrid-2-yl)4-piperidinylamino-1-(4-hydroxy-phenoxy)-2-propanol The product of the previous step is hydrogenated using the procedure described in example 9b. The reaction product is purified by flash chromatography, eluting with a 95:5 mixture of methylene chloride and methanol. The named compound melting at 135–137° C. is obtained; [$\alpha_D$]=5.64 (C=1% CH$_3$OH).

Example 26

26a)3-[1-(5-Ethoxycarbonylpyrid-2-yl)-4-piperidinylamino-1-(4-benzyloxy-3-methylsulfinyl)-phenoxy)-2-propanol 0.75 g (0.002 mole) of 4-benzyloxy-3-methylsulfinyl-1-(2,3 epoxypropoxy) benzene (prepared using the process described in U.S. Pat. No. 4,396,629) is mixed with 0.646 g (0.0026 mole) of the basic product of example 4 in absolute ethanol. The mixture is heated under reflux for 4 hours, then dried and the reaction product purified by chromatography, eluting with mixtures of CH$_2$Cl$_2$, CH$_3$OH and concentrated NH$_4$OH in proportions variable between 95:5:0.2 and 90:10:1. The reaction product melting at 113–130° C. is obtained.

26b)3-[1-(5-Ethoxycarbonylpyrid-2-yl)-4-piperidinylamino-1-(4-hydroxy-3-methylsulfinyl)-phenoxyl-2-propanol and it Dihydrated Hydrochloride The product of the previous step is heated for 7 hours at 55° C. in 20 ml of CF$_3$COOH. The solvent is partially evaporated, ethyl acetate and toluene added, and more solvent evaporated off. Water saturated with Na$_2$CO$_3$ is added and an extraction with ethyl acetate carried out. The reaction product is dried and purified by flash chromatography, eluting with a mixture of CH$_2$Cl$_2$, CH$_3$OH and concentrated NH$_4$OH in proportions varying between 92:8:0.8 and 90:10:1. The named compound is obtained as a free base (melting point: 95–100° C.). The product is dissolved in acetone, a solution of HCl in isopropanol is added, filtered and washed with acetone. The named product is obtained M. P. 173–175° C.

Example 27

4-ter-Butoxycarbonylamino-1-(5-methylpyrid-2-yl)-piperidine 2.03 g (0.0101 mole) of the product of preparation 1 is heated overnight at 130° C. with 3.5 g (0.0203 mole) of 2-bromo-5-methylpyridine and 1.5 ml of triethylamine in 50 ml of dimethylsulphoxide. The mixture is poured into water and the reaction product extracted and purified by flash chromatography (using a ⅓ mixture of cyclohexane and ethyl acetate). Melting point: 121–123° C.

Example 28

4-Amino-1-(5-methylpyrid-2-yl)-piperidine and its Hydrated Hydrochloride

A solution containing the product of example 27 in 18 ml of ethyl acetate and 18 ml of HCl in ethyl acetate (about 3N) is heated under reflux for 4 hours. The mixture is filtered and washed in acetone. Crystallising in isopropanol produces the named compound with a melting point of 281–283° C.

Example 29

29a)3-[1-(5-Methylpyrid-2-yl)4-piperidinylamino-1-(4-benzyloxyphenoxy)-2-propanol 1.81 g (0.00956 mole) of the product of example 28 and 2.2 g (0.00860 mole) of 4-benzyloxy-1-(2,3-epoxypropoxy)-benzene in 100 ml of absolute ethanol are heated overnight under reflux. The solvent is evaporated off and the reaction product purified by flash chromatography, eluting with a 6/4 mixture of cyclohexane and ethyl acetate and then a 100/1 mixture of methanol and ammonia. The named product is obtained, melting at 123–125° C.

29b)3-[1-(5-Methylpyrid-2-yl)-4-piperidinylamino-1-(4-hydroxyphenoxy)-2-propanol and its Hydrochloride The procedure is as described in 29b but using the product of example 29a. The reaction product is purified by flash chromatography, eluting with a 4/6 mixture of ethyl acetate and methanol. The named compound is obtained as a base. The hydrochloride is prepared by adding HCl in isopropanol. M. P.: 151–153° C.

Example 30

4-ter-Butoxycarbonylamino-1-(5-methoxycarbonyl-pyrid-2-ylmethyl)-piperidine

A solution containing 0.7 g (0.0034 mole) of the product of preparation 1, 0.53 g (0.0023 mole) of 2-bromomethyl-5-methoxycarbonyl-pyridine (prepared using the procedure described in J. Med. Chem., 1992, 3, 490–501), and 0.26 ml (0.0025 mole) of triethylamine in 10 ml of dimethylformamide is heated at 40° C. for 2 hours. It is then poured into water, extracted with ethyl acetate and the reaction product purified by flash chromatography (eluant: ethyl acetate). The named compound is obtained: M. P. 110–112° C.

Example 31

4-Amino-1-(5-methoxycarbonyl-pyrid-2-ylmethyl)-piperidine

The product of example 30 is heated for 3 hours at 40° C. in a solution of CH$_2$Cl$_2$ containing 11 ml of CF$_3$COOH. The solvent is evaporated off and the substance crystallised in acetone. The named product is obtained: M. P. 173–175° C.

Example 32

3-[1-(5-Methoxycarbonyl-pyrid-2-ylmethyl)-4-piperidinylamino-1-(4-hydroxyphenoxy)-2-propanol The procedure is as described in example 12 but using the product of example 31 instead of the product of example 6. The named product is obtained: M. P. 141–143° C.

Example 33

4-ter-Butoxycarbonylaminomethyl-1-(5-methoxycarbonyl-pyrid-2-ylmethyl)-piperidine

1.68 g (0.0078 mole) of the product of preparation 2, 1 ml (0.0068 mole) of triethylamine and 1.5 g (0.0065 mole) of 2-bromomethyl-5-methoxycarbonyl-pyridine are heated for 2 hours in 25 ml of dimethylformamide. The mixture is poured into water, extracted with ethyl acetate, washed in water and then the product dried. Crystallisation in isopropyl ether gives the product: M. P. 103–105° C.

Example 34

4-Aminomethyl-1-(5-methoxycarbonyl-pyrid-2-ylmethyl)-piperidine Trifluoracetate

A solution containing 1.7 g (0.0046 mole) of the product of example 33, 15 ml of $CF_3COOH$ and 15 ml of $CH_2Cl_2$ is heated at 40° C. for 3 hours. The solvent is evaporated off under vacuum, concentrated ammonia is added, and then an extraction with ethyl acetate carried out. The solvent is evaporated off and the named product obtained: M. P. 193–195° C.

Example 35

3-1-(5-Methoxycarbonyl-pyrid-2-ylmethyl)-piperidinylaminomethyl]-1-(4-hydroxyphenoxy)-2-propanol

The procedure is as described in example 9 but using the product of example 34 instead of the product of example 32. The named compound is obtained.

Example 36

(2R)-3-(5-Ethoxycarbonylpyrid-2-yl)-4-piperidinylamino]-1-(4-hydroxy-phenoxy)-2-propanol

By proceeding as described in example 25 but using (2R)-4-benzyloxy-1-(2,3-epoxypropoxy) benzene instead of (2S)-4-benzyloxy-1-(2,3-epoxypropoxy) benzene the named compound is obtained. MP: 134–135° C. $[\alpha?_D[=+4.20$ (C=1% $CH_3OH$).

Example 37

(2S)-4-Benzyloxy-3-methylsulfinyl-1-(2,3-epoxypropoxy) Benzene

0.71 g of 60% NaH (0.0177 mole) is dissolved with stirring under a nitrogen atmosphere in 15 ml of dimethylformamide. Then 4.45 g (0.0169 mole) of (2S)-4-benzyloxy-3-methylsulfinylphenol (prepared according to the procedure described in U.S. Pat. No. 4,936,629) in 35 ml of dimethylformamide is added slowly (over 30 minutes) followed by 4.40 g (0.0169 mole) of S(+)glycidylnosilate in 10 ml of dimethylformamide. After adding the last reagent the mixture is left to react at room temperature for 3 hours. Water is added, an extraction with ethyl acetate carried out and then the solvent evaporated off. The reaction product is purified by flash chromatography, eluting with a 97/3 mixture of $CH_2Cl_2$ and MeOH. $[\alpha_{365nm}=-14.3°; [\alpha]_{436\,nm}=-39°$ (C=1% $CH_3OH$, t=20° C.) the named compound is obtained.

The product obtained in this way is subjected to HPLC analysis under the following conditions:

stationary chiral phase CHIRALCEL OD-H mobile phase: hexane/ethanol=80/20 (0.5 ml/min).

Two peaks are seen and $TR_1$=20.780 min and $TR_2$=23.900 min corresponding to the diastereoisomers having different configurations from the sulphur atom.

Example 38

38a)(2S) 3-[1-(5-Ethoxycarbonylpyrid-2-yl)4-piperidinylamino-1-(4-benzyloxy-3-methylsulfinyl)-phenoxy]-2-propanol

The product of example 37, and 3.82 g (0.0153 mole) of the product of example 4 in the form of a base, in 60 ml of ethanol, are heated overnight under reflux. The solvent is evaporated off and the reaction product purified by flash chromatography, eluting with a 97/3 mixture of $CH_2Cl_2$ and methanol. The required product is obtained, melting at 109–110° C.

This product is subjected to HPLC analysis under the following conditions:

stationary chiral phase: CHIRALCEL OD-H mobile phase: hexane/ethanol=65/35–(0.6 ml/min, 660 psi).

Two peaks are seen, $TR_1$=20.687 min and $TR_2$=28.327 min, corresponding to the diastereoisomers having different configurations from the sulphur atom.

38b)(2S) 3-[1-(5-Ethoxycarbonylpyrid-2-yl)-4-piperidinylamino-1-(4-hydroxy-3-methylsulfinyl)-phenoxy]-2-propanol and its Hydrated Dihydrochloride

The product obtained in example 38a) is heated with 100 ml of $CF_3COOH$ for 6 hours at 55° C. The solvent is evaporated off and water saturated in $Na2CO_3$ is added, together with ice.

The mixture is then extracted with ethyl acetate, washed with water and the solvent evaporated off. The reaction product is purified by flash chromatography, eluting with a 9/1 mixture of $CH_2Cl_2$ and methanol. The required product is obtained, melting at 62–65° C. The hydrated dihydrochloride is prepared using a solution of HCl in isopropanol (MP 172–174° C.). $[\alpha]_D=+4.0°$; $[\alpha]_{436}nm=+11.7°$ C.; $[\alpha]546_{nm}=5.1°$; (C=1% methanol). The basic product is subjected to HPLC analysis under the following conditions:

stationary chiral phase: CHIRALCEL OD-H mobile phase: isopropanol (0.4 ml/min, 1880 psi).

Two peaks are seen and $TR_1$=11.900 min and $TR_2$=13.713 min corresponding to the diastereoisomers having different configurations from the sulphur atom.

38c) Separation of the Diastereoisomers of 38b)

The product of the previous example was subjected to preparatory chiral HPLC to separate the diastereoisomers under the following conditions:

Apparatus: PROCHROM LC 50 with dynamic axial compression. Column diameter 50 mm. Length of stationary phase: 30 cm.

Stationary phase: CHIRALCEL OD 390 g of OD chiralcel phase are suspended in 200 ml of propanol and compressed to 20 bar.

Mobile phase: 91/9 isohexane/ethanol+0.1% $CF_3COOH$+0.1% triethylamine.

Two products are separated out which, after evaporation of the mobile phase, show a considerable weight excess owing to the formation of salts. These salts were eliminated by reverse phase purification as follows:

Apparatus: PROCHROM LC 50
Stationary phase: KROMASIL C18 100 Å10 μm 380 g of stationary phase are suspended in 560 ml of methanol and compressed to 40 bar.
Mobile phase: Eluant A: $H_2O+0.1\%$ $CF_3COOH$/Eluant B: $CH_3CN/H_2O=90/10+0.8\%$ $CF_3COOH$. Elution gradient

| | Elution gradient | |
|---|---|---|
| T (in min) | % A | % B |
| 0 | 90 | 10 |
| 5 | 90 | 10 |
| 50 | 67 | 33 |
| 60 | 67 | 33 |

The two purified products were analysed by HPLC on chiral under the following conditions:
stationary chiral phase: CHIRALCEL OD
mobile phase: 85/15 isohexane/ethanol+0.1% $CF_3COOH$+0.1% triethylamine.
These two products, corresponding to the diastereoisomers having a different configuration from the sulphur atom show relative retention times $TRR_1=1$ and $TRR_2=1.12$. Mass spectrometry confirmed that the two products obtained have the same mass, i.e., $MH^+=478$ and that their characteristic fragmentation is the same.

Example 39

4-Hydroxy-3-methylcarbonyl-1-(2,3-epoxypropoxy) Benzene

A solution containing 3.00 g (0.020 mole) of 2,5-dihydroxyacetophenone, 3.37 ml (0.040 mole) of epibromhydrine and 5.06 g (0.040 mole) of $K_2CO_3$ in 30 ml of acetone are heated for 8 hours under reflux. The solvent is evaporated off, 20 ml of a saturated solution of $NaH_2PO_4$ and 120 ml of water are added, and an extraction carried out with ethyl acetate.

The solvent is evaporated off and the reaction product purified by chromatography, eluting with a mixture of $CH_2Cl_2$ and ethyl acetate in proportions varying between 100/0 and 95/5. The required product is obtained, MP: 83–135° C.

Example 40

4-Benzyloxy-3-methylcarbonyl-1-(2,3-epoxypropoxy) Benzene

A solution containing 1 g (0.0048 mole) of the product of example 39, 0.856 ml (0.00072 mole) of benzyl bromide and 0.924 g (0.0072 mole) of $K_2CO_3$ in 12 ml of acetone are heated for 6 hours under reflux in nitrogen. Then 0.5 ml (0.0042 mole) of benzyl bromide are added and the mixture heated for a further 7 hours. The substance is poured into water, extracted with ethyl acetate and the solvent evaporated off . The reaction product is purified by chromatography, eluting with an 8/2 mixture of hexane and acetone. The required product is obtained, MP: 45–48° C.

Example 41

3-[1-(5-Ethoxycarbonylpyrid-2-yl)-4-piperidinylamino]-1-(4-hydroxy-3-methylcarbonyl)-phenoxy]-2-propanol By proceeding as described in example 9 but using the product of example 40 instead of the 4-benzyloxy-1-(2,3-epoxyproxy)-benzene, the required product is obtained, MP: 105–108° C.

Example 42

(1-Methylcarbonyl-3-bromo4-benzyloxy)-benzene

A solution containing 0.92 g (0.428 mole) of (2-bromo-4-methylcarbonyl)-phenol, 51 ml (0.428 mole) of benzyl bromide, 64 g of NaI (0.043 mole) and 89.0 g (0.642 mole) of $K_2CO_3$ in 1.5 l of acetone is heated for 4 hours under reflux. The mixture is filtered, the solvent evaporated off, ethyl acetate added and the mixture washed with water. The solvent is evaporated off and the required product is obtained, MP: 117–119° C.

Example 43

(3-Bromo-4-benzyloxy-1-acetoxy)-benzene

A solution containing 93 g (0.3 mole) of the product of example 42 and 259 g (1.05 mole) of 3-chloro-perbenzoic acid (concentration 70%) in 2 l of $CH_2Cl_2$ is heated for 24 hours under reflux. The solvent is evaporated off, ethyl acetate added, and the mixture washed with a solution of $Na_2S_2O_5$. The mixture is filtered and the solvent evaporated off. The required compound is obtained, MP: 69–71° C.

Example 44

(4-Benzyloxy-3-(2-furyl) Phenol

A solution of 180 ml of dioxane containing 13 g (0.0406 mole) of the product of example 43, 5 g (0.0447 mole) of 2-furanboronic acid, 1.6 g of Tetrakis (triphenylphosphine)-palladium and 38.3 g (0.1215 mole) of tetrabutylammonium fluoride is heated under an argon atmosphere for 5 hours at 90° C. 1 l of ethyl ether is added and the mixture washed with water.

The mixture is filtered and the solvent evaporated off. The reaction product is purified by chromatography (eluant: cyclohexane/ethyl acetate=8/29). The required compound is obtained MP: 112–115° C.

Example 45

(4-Benzyloxy-3-fur-2yl-1-(2,3-epoxypropoxy)]-benzene 8.3 g (0.031 mole) of the product of the previous step together with 6.5 g (0.046 mole) of $K_2CO_3$ in 60 ml of dimethylformamide is stirred for 15 minutes at room temperature. After 15 minutes, 5.3 ml (0.062 mole) of epibromhydrine is added and the mixture heated for 6 hours at 70° C. This is then poured into a mixture of water and ice and extracted with ethyl acetate. The substance is filtered and the solvent evaporated off. The reaction product is purified by chromatography, eluting with an 85/15 mixture of cyclohexane and ethyl acetate and then with a 9/1 mixture of cyclohexane and ethyl acetate. The required product is obtained, MP: 62–64° C.

Example 46

3-[1-(5-Ethoxycarbonylpyrid-2-yl)-4-piperidinylamino]-1-(4-hydroxy-3-(2-furyl)-phenoxyl-2-propanol and its Hydrated Dihydrochloride We proceed as described in example 26 but using the product of example 45 instead of the 4-benzyloxy-3-methylsulfinyl-1-(2,3-epoxypropoxy) benzene. The benzyl group is split off by hydrogenisation in ethyl acetate. The reaction product is purified by chromatography, eluting with an 85/15 mixture of ethyl acetate and methanol. The hydrochloride is prepared in isopropanol. The required product is obtained, MP: 251–253° C.

Example 47

3-Bromo4-benzyloxy)-phenol 0.5 g (0.0155 mole) of the product of example 43 together with 18.7 ml (0.0187 mole) of 1N NaOH in 150 ml of methanol are reacted at room temperature for 40 minutes while stirring. Citric acid is added to give a pH of 6 and the solvent evaporated off. Ethyl acetate is added, the mixture washed with water and the solvent evaporated off. The required compound is obtained, MP: 61–63° C.

Example 48

3-Bromo-4-benzyloxy)-1-(2,3-epoxypropoxy)-benzene 3.5 g (0.0125 mole) of the product of example 47, 18.8 ml (0.0188 mole) of 1N NaOH and 2.2 ml (0.025 mole) of epibromhydrine in 50 ml of dioxane are heated overnight at 45° C. The solvent is evaporated off, water added, the mixture extracted with ethyl acetate and the solvent evaporated off. The reaction product is purified by chromatography (cyclohexane/ethyl acetate=8/2). The required compound is obtained.

Example 49

3-[1-(5-Ethoxycarbonylpyrid-2-yl)-4-piperidinylamino]-1-(3-bromo-4-hydroxy)phenoxy]-2-propanol The product of example 48 is reacted with the product of example 4 (base), using the process described in 9a. The product of that reaction is treated with $CF_3COOH$ for 4 hours at 55° C. The reaction product is purified by chromatography ($CH_2Cl_2/CH_3OH=93/7$). The product is crystallised in isopropanol. MP: 123–126° C.

Example 50

4-Benzyloxy-3-(N-ter-butoxycarbonyl-N-methylsulfonyl)-amino-1-(2,3,-epoxypropoxy)-benzene A solution containing 1 g (1.0025 mole) of 4-phenylmethoxy-3-[N-ter-butoxycarbonyl-N-methansulfonyl)-amino]-phenol (prepared using the process described in WO 9604233), 0.75 g (0.0029 mole) of glycidylnosilate and 1.1 g (0.008 mole) of $K_2CO_3$ is heated for 24 hours under reflux. The mixture is filtered, the solvent evaporated off, and the reaction product purified by chromatography, eluting with a 7/3 mixture of cyclohexane and ethyl acetate.

Example 51

51a)3-[1-(5-Ethoxycarbonylpyrid-2-yl)-4-piperidinylamino]-1-(4-benzyloxy-3-methansulfonamido)-phenoxy]-2-propanol 0.77 g (0.00172 mole) of the product of example 50, 0.86 g (0.0035 mole) of the product of example 4 (base) and 0.2 g of $LiClO_4$-in 50 ml of acetonitrile is reacted at room temperature for 48 hours with stirring. The mixture is heated for 9 hours at 40° C. and then the reaction is stopped. The solvent is evaporated off and then 30 ml of $CH_2Cl$ and a 3 N solution of HCl in ethyl acetate (20 ml) are added. The mixture is heated for 4 hours at 40° C. to evaporate off the solvent. The mixture is washed with ammonia and then extracted with ethyl acetate. The solvent is evaporated off and the reaction product purified by flash chromatography, eluting with a 9/1 mixture of $CH_2Cl_2/CH_3OH$. The required product is obtained MP: 112–114° C.

51b)3-[1-(5-Ethoxycarbonylpyrid-2-yl)4-piperidinylamino]-1-(-4-hydroxy-3-methansulfonamido)-phenoxy]-2-propanol The product of example 51a is hydrogenated using the process described in example 9b, operating at a pressure varying between ambient and 50 psi. The reaction product is purified by flash chromatography ($CH_2Cl/CH_3OH=9/1$). The required product is obtained MP: 77–80° C.

Example 52

4-Acetylamino-1-(5-chloropyrid-2-yl)-piperidine 6.7 g (0.035 mole) of 2-bromo-5-chloropyridine, 4.97 g (0.035 mole) of 4 acetylamino-piperidine and 4.83 g (0.035 mole) of $K_2CO_3$ in 50 ml of amyl alcohol are heated for 24 hours under reflux. The solvent is evaporated off, water is added, and the mixture extracted using $CH_2Cl_2$. The required product is obtained MP: 196–198° C.

Example 53

4-Amino-1-(5-chloropyrid-2-yl)-piperidine and its Dihydrochloride 5.5 g (0.022 mole) of the product of example 52 in 25 ml of 6 N HCl is heated for 5 hours under reflux. The solvent is evaporated off, 50 ml of water added, together with a solution of NaOH until the pH is basic. The mixture is extracted using $CH_2Cl_2$, and the solvent evaporated off. The hydrochloride is prepared in isopropanol, and crystallised in methanol. The required product is obtained MP: 295° C.

Example 54

3-[1-(5-Chloropyrid-2-yl)-4-piperidinylamino]-1-(4-hydroxyphenoxy)-2-propanol

We proceed as described in example 12 but using the product of example 53 (base) instead of the product of example 6. Following the treatment with $CF_3COOH$ the mixture is evaporated, ethyl acetate added and the mixture washed with a solution of $NaH_2PO_4$ until the pH is 5. The solvent is evaporated off and the reaction product purified by flash chromatography, eluting with a 9/1 mixture of $CH_2Cl_2$ and methanol. The required product is obtained MP: 148–150° C.

Example 55

2-Chloro-6-ethoxycarbonyl-pyridine 14.1 g (0.0895 mole) of 2-chloro-6-hydroxycarbonylpyridine in 133 ml of a solution of HCl in ethanol is heated for 8 hours under reflux. The solvent is evaporated off, ethyl acetate added and the mixture washed with a solution of bicarbonate. The solvent is further evaporated and the reaction product purified by flash chromatography (cyclohexane/ethyl acetate=7/3). The required product is obtained.

Example 56

4-ter-Butoxycarbonylamino-1-(6-ethoxycarbonylpyrid-2-yl)-piperidine

A solution containing 1.17 g (0.0063 mole) of the product of example 55, 1.27 g (0.0063 mole) of the product of preparation 1, 0.9 ml of triethylamine and NaI in 34.2 ml of dimethylformamide are heated for 24 hours at 80° C. This is poured into water, extracted with ethyl acetate and the solvent evaporated off. The reaction product is purified by flash chromatography, eluting with a 7/3 mixture of cyclohexane and ethyl acetate.

Example 57

4-Amino-1-(6-ethoxycarbonylpyrid-2-yl)-piperidine and its Hydrochloride 0.99 g (0.0025 mole) of the product of example 56 in 6 ml of ethyl acetate and 6 ml of a solution HCl in ethyl acetate are heated for 8 hours under reflux. The mixture is filtered, and washed with acetone, ammonia is added and the mixture extracted with ethyl acetate. The reaction product is purified by chromatography, eluting with a 100/1 mixture of $CH_3OH$ and $NH_4OH$. The required product is obtained.

Example 58

58a)3-[1-(6-Ethoxycarbonyl-pyrid-2-yl)-4-piperidinylamino]-1-(4-benzyloxy phenoxy)-2-propanol 0.3 g (0.0012 mole) of the product of example 57 (base), 0.292 g (0.00114 mole) of (4-benzyloxy-1-(2,3-epoxypropoxy) benzene in 15 ml of ethanol are heated overnight under reflux. The mixture is evaporated under reduced pressure and the reaction product purified by chromatography, eluting with a 9/1 mixture of $CH_3OH$ and ethyl acetate.

58b)3-[1-(6-Ethoxycarbonyl-pyrid-2-yl)-4-piperidinylamino]-1-(4-hydroxy-phenoxy)-2-propanol By proceeding as described in example 9b, the required compound is obtained MP: 200–201 ° C.

Example 59

59a)(2S)3-[5-Aminocarbonyl-pyrid-2-yl)4-piperidinylamino]-1-(4-benzyloxy-3-methylsulfinyl-phenoxy)-2-propanol 1 g (0.00314 mole) of the product of example 37 and 0.83 g (0.00377 mole) of the product of example 2 in base form are heated for 6 hours in a nitrogen atmosphere under reflux. The solvent is evaporated off and the reaction product purified by chromatography, eluting with a 90/10/1 mixture of $CH_2Cl_2$, methanol and $NH_4OH$. The required product is obtained MP: 143–147° C.

The product thus obtained is subjected to HPLC analysis under the following conditions:

stationary chiral phase: CHIRALCEL OD-H mobile phase: hexane/ethanol=20/809 (0.4 ml/min).

Two peaks are seen, $TR_1$=17.040 min, $TR_2$=19.827 min corresponding to the diastereoisomers having different configurations from the sulphur atom.

59b)(2S)3-[5-Aminocarbonyl-pyrid-2-yl)-4-piperidinylamino]-1-(4-benzyloxy-3-methylsulfinyl-phenoxy)-2-propanol We proceed as described in example 38b) but using the product of example 59a) instead of the product of example 38a). The reaction product is purified first by chromatography, eluting with a $CH_2Cl_2$/methanol/$NH_4OH$ mixture =85/15/1.5 and then 80/20/2. This is followed by a second chromatography, eluting with an 80/20 mixture of ethyl acetate and methanol and then using a $CH_2Cl_2$/methanol/$NH_4OH$ mixture =85/15/1.5 and then 80/20/2. The required product is obtained MP: 74° C.

The product obtained in this way is subjected to HPLC analysis under the following conditions:

stationary chiral phase: CHIRALCEL OD-H mobile phase: hexane/ethanol=65/35-(0.6 ml /min).

Two peaks are seen, $TR_1$=13.900 min, $TR_2$=18.233 min corresponding to the diastereoisomers having different configurations from the sulphur atom.

Example 60

3-[1-(5-Hydroxycarbonyl-pyrid-2-yl)-4-piperidinylamino]-1-(4-hydroxy-3-methylsulfinyl)-2-propanol 0.48 g (0.001 mole) of the product of example 26b, 2.51 ml of 1 N NaOH (00025 mole), 2.5 ml of water and 2.5 ml of ethanol are mixed at room temperature. After 24 hours the ethanol is evaporated off and 0.144 ml of acetic acid (d=1.049, 0.0025 mole) is added. An oil is seen to form. The water is eliminated and 10 ml of ethanol added. The solvent is evaporated off and more ethanol added. This operation is repeated several times. The required product is obtained MP: 215–217° C.

Example 61

(3-Acetylamino-4-benzyloxy-1-acetoxy)-benzene 2 g (0.0077 mole) of (3-amino-4-benzyloxy-1-acetoxy)-benzene (prepared using the process described in Synt. Commun. 22; 20; 1992; 2877–2882) is dissolved while stirring in 150 ml of $CH_2Cl_2$. 1.3 ml of triethylamine (0.0093 mole) is added and then 0.8 ml (0.0085 mole) of acetic anhydride. The mixture is left overnight and then heated for 4 hours under reflux. It is washed with water, filtered and the solvent evaporated off. Cyclohexane is added and the mixture filtered. The required product is obtained MP: 105–107° C.

Example 62

3-Acetylamino-4-benzyloxy-phenol 3 g (0.010 mole) of the product of the previous step are dissolved in 120 ml of methanol and 30 ml of water. 12 ml of 1 N NaOH (0.012 mole) are added and the mixture stirred for 30 minutes at room temperature. Citric acid is added until the pH is 6, the solvent evaporated off, ethyl acetate added and mixture washed with water. It is then filtered and dried. The required product is obtained.

Example 63

3-Acetylamino-4-benzyloxy-1-)2,3-epoxypropoxy)-benzene 0.5 g (0.0019 mole) of the product of example 62 is mixed while stirring at room temperature for 15 minutes. With 0.4 g of $K_2CO_3$ (0.0029 mole) in 5 ml of dimethylformamide. After 15 minutes, 0.32 ml (0.0038 mole) of epibromhydrine is added and this is allowed to react overnight. The mixture is poured into water, extracted with ethyl acetate, dried and filtered. The reaction product is purified by chromatography, eluting with a 6/4 mixture of cyclohexane and ethyl acetate. The required product is obtained.

Example 64

64a)3-[1-(5-Ethoxycarbonyl-pyrid-2-yl)-4-piperidinylamino]-1-(3-piperidinylamino]-1-(3-acetylamino4-benzyloxy)-phenoxy)-2-propanol 64a)0.22 g (0.0007 mole) of the product of example 63 is heated overnight under reflux with 0.175 g (0.0007 mole) of the product of example 4 in base formn in 10 ml of ethanol. The solvent is evaporated off and the product purified by flash chromatography, eluting with methanol. The solvent is evaporated again and the required product is obtained MP: 125–126° C.

64b)3-[1-(5-Ethoxycarbonyl-pyrid-2-yl)-4-piperidinylamino]-1-(3-acetylamino-4-hydroxy)-phenoxy)-2-propanol The product of example 64a is hydrogenated using the process described in example 9b. The required product is obtained MP: 103–105° C.

Example 65

(3-Methylsulfonyl-4-benzyloxy-1-phenylcarbonyloxy)-benzene 3.26 g (0.0089 mole) of (3-methylsulfonyl-4-benzyloxy-1-phenylcarbonyloxy)-benzene are dissolved in 30 ml of acetone and 5 ml of methanol; at a temperature of between 5 and 10° C. Then 2.86 g of magnesium monoperoxyphthalate (MMPP) (purity 80%, 0.0046 mole) dissolved in 20 ml of methanol is added. After 3.5 hours a further 0.3 g (0.00048 mole) of MMPP in I ml of ethanol is added. This is allowed to react overnight at room temperature. 50 ml of water and 5 ml of a saturated solution of $NaHCO_3$ are added and the mixture extracted with ethyl acetate. The solvent is evaporated off and the required product obtained MP: 142–145° C.

Example 66

3.09 g (0.008 mole) of the product of example 65 is dissolved in 40 ml of THF and 10.5 ml of 1 NaOH (0.010 mole) are added. After 4 hours, 25 ml of water and enough $NaH_2PO_4$ to give a pH of 7 are added and the mixture extracted with methyl acetate. It is washed with aqueous solutions of $NaHCO_3$ and NaCl and the solvent evaporated off. The required product is obtained MP: 154–156° C.

Example 67

4-Benzyloxy-3-methylsulfonyl-1-)2,3-epoxypropoxy)-benzene 0.158 (0.00395 mole) of NaOH in 10 ml of DMF are stirred for 10 minutes and then 1 g (0.00359 mole) of the phenol obtained in example 66 is added. After 10 minutes 0.977 g (0.00377 mole) of glycidylnosilate in 5 ml of DMF is added and the mixture left to react at room temperature for 24 hours. 100 ml of water and 2 ml of a solution of $NaH_2PO_4$ are added, the mixture extracted with ethyl acetate and washed with water. The reaction product is purified by chromatography, eluting with a $CH_2Cl_2$/ethyl acetate mixture in proportions of 98/2 and then 97/3 and 96/4. The required product is obtained MP: 78–82° C.

Example 68

68a)3-[1-(5-Ethoxycarbonyl-pyrid-2-yl)-4-piperidinamino]-1-(4-benzyloxy-3-methylsulfonyl)-phenoxy]-2-propanol 0.700 g (0.00209 mole) of the product of example 67 and 0.574 g (0.0023 mole) of the product of example 4 in base form in 6 ml of ethanol are heated for 6 hours under reflux. The solvent is evaporated off, ethyl acetate is added to the oil formed and the product is allowed to crystallise. The required product is obtained MP: 111–114° C.

68b) 3-[1-(5-Ethoxycarbonyl-pyrid-2-yl)-4-piperidinamino]-1-(4-hydroxy-3-methylsulfonyl)-phenoxyl-2-propanol The product of the previous step is treated with $CF_3COOH$ using the process described in example 26b, the product being purified by flash chromatography, eluted with a 90/10/1 mixture of $CH_2Cl_2$, MeOH and concentrated NH3. The required product is obtained.

Example 69

3-[1-(6-Chloro-pyrid-2-yl)-4-piperidinylamino]-1-(4-hydroxy-3-methylsulfonamido)-phenoxy]-2-propanol The product of example 50 is reacted with 4-amino-1-(6-chloropyrid-2yl)-piperidine (prepared as described in EP 21973) using the process described in example 51. The required product is obtained.

Example 70

3-[1-(5-Ethoxycarbonylpyrid-2-yl)-4-piperidinylamino]-1-(4-hydroxy-3-methansulfonamido)-phenoxy]-2-propanol The product of example 50 is reacted with the product of example 57 (base) under the conditions described in example 51. The required product is obtained.

Example 71

3-[1-(6-Chloropyrid-2-yl)4-piperidinylamino]-1-(4-hydroxyphenoxy)-2-propanol

By proceeding as described in example 58 but using 4-amino-1-(6-chloropyrid-2yl) piperidine instead of the product of example 57 the required product is obtained.

What is claimed is:

1. A compound of formula (Ia):

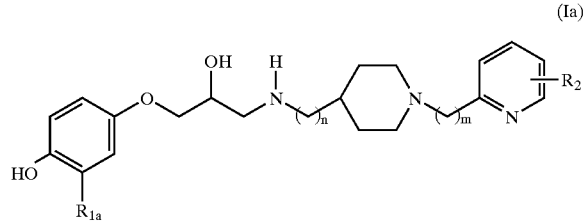

wherein $R_{1a}$ represents hydrogen, an $—S(O)_z—(C_1–C_4)Alk$ group, a $—CO(C_1–C_4)Alk$ group, an $—NHSO_2—(C_1–C_4)Alk$ group, an $NHCO (C_1–C_4) Alk$ group, a 2-furyl group or a halogen;

$R_2$ represents hydrogen or a $(C_1-C_4)$Alk group, a $(C_1-C_4)$ alkoxyl group, a halogen, —COOH, —COO$(C_1-C_4)$Alk, —CN, —CONR$_3$R$_4$, —NO$_2$, —SO$_2$NH$_2$, —NHSO$_2$(C$_1$-C$_4$)Alk;

m and n are independently 0, 1 or 2;

$R_3$ and $R_4$ independently represent hydrogen or a $(C_1-C_4)$ Alk group;

Z is 1 or 2 and their salts or solvates.

2. A compound of formula (I)

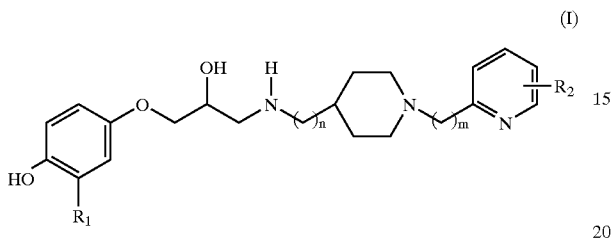

(I)

wherein $R_1$ represents hydrogen, an —S(O)$_z$—(C$_1$-C$_4$)Alk group, a —CO(C$_1$-C$_4$)Alk group, or an —NHSO$_2$—(C$_1$-C$_4$) Alk group;

$R_2$ represents hydrogen or a $(C_1-C_4)$Alk group, a $(C_1-C_4)$ alkoxyl group, a halogen, —COOH, —COO$(C_1-C_4)$Alk, —CN, —CONR$_3$R$_4$, —NO$_2$, —SO$_2$NH$_2$, or —NHSO$_2$(C$_1$-C$_4$)Alk;

m and n are independently 0, 1 or 2;

$R_3$ and $R_4$ independently represent hydrogen or a $(C_1-C_4)$ Alk group;

Z is 1 or 2 and their salts or solvates.

3. A compound according to claim 1 wherein $R_2$ is in position 5 or 6 of the pyridine.

4. A compound according to claim 1 where n and m are zero.

5. A compound according to claim 1 for wherein the $(C_1-C_4)$Alk group is a methyl or ethyl group.

6. A compound according to claim 1 wherein $R_2$ is one of the following: —COOH, —COO(C$_1$-C$_4$)Alk, —CN, —NO$_2$, —CONR$_2$R$_3$ or —NHSO$_2$—(C$_1$-C$_4$)Alk.

7. A compound according to claim 1 wherein $R_2$ is a halogen.

8. A process for preparing a compound of formula (Ia) of claim 1 wherein a compound of formula (II) is reacted

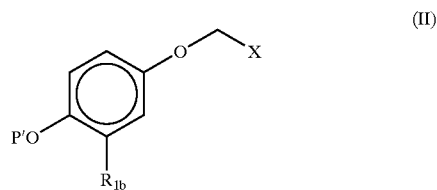

(II)

wherein $R_{1b}$ is $R_{1a}$ as indicated in claim 1, P' is a protective group and X is a group with formula (a) or (b)

(a)

-continued

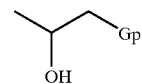

(b)

where Gp is a starting group with an amine of formula (III)

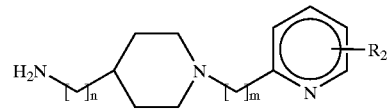

(III)

wherein n, m and $R_2$ are as indicated in claim 1, with the P' group split off and the compound of formula (Ia) thus obtained converted as appropriate into one of its salts.

9. A compound of formula (VII)

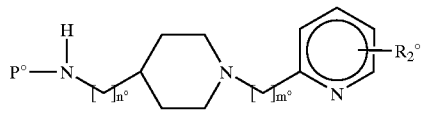

(VII)

wherein

P° is hydrogen or a protective group; n° and m° are 0, 1 or 2;

$R_2°$ is (C$_1$-C$_4$)Alk; (C$_1$-C$_4$)alkoxyl, —COOH, —COO (C$_1$-C$_4$)Alk, —CN, NO$_2$, —CONR$_3°$, R$_4°$,—SO$_2$NH$_2$, —NHSO$_2$(C$_1$-C$_4$)Alk;

$R_3°$ and $R_4°$ are hydrogen or a (C$_1$-C$_4$)Alk group; on condition that: when n° and m° are zero, $R_2°$ is other than methoxy in position 6 and halogen in position 3 or 6 of the pyridine; when n° is 1, m° is 0, $R_2°$ is other than chlorine in position 6 of the pyridine and when n° is 0, m° is 0 or 1, $R_2°$ is other than methyl.

10. A compound according to claim 2 wherein $R_2$ is in position 5 or 6 of the pyridine.

11. A compound according to claim 2 wherein n and m are zero.

12. A compound according to claim 2 wherein the (C$_1$-C$_4$)Alk group is a methyl or ethyl group.

13. A compound according to claim 2 wherein $R_2$ is one of the following:

—COOH, —COO(C$_1$-C$_4$)Alk, —CN, —NO$_2$, —CONR$_2$R$_3$ or —NHSO$_2$(C$_1$-C$_4$)Alk.

14. A compound according to claim 2 wherein $R_2$ is a halogen.

15. A process for preparing a compound of formula I of claim 2 wherein a compound of formula (II) is reacted

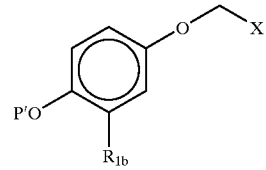

(II)

wherein $R_{1b}$ is $R_1$ as indicated in claim 2, P' is a protective group and X is a group with formula (a) or (b)

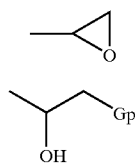

(a)

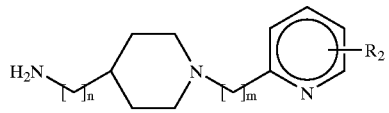

(b)

where Gp is a starting group with an amine of formula (III)

(III)

$$H_2N \underset{n}{\diagdown} \text{[piperidine]} \underset{m}{\diagdown} \text{[pyridine]} - R_2$$

wherein n, m and $R_2$ are as indicated in claim 2, with the P' group split off and the compound of formula (I) thus obtained converted as appropriate into one of its salts.

16. A pharmaceutical composition comprising a compound according to claim 1 together with a pharmaceutical excipient.

17. A pharmnaceutical composition comprising a compound according to claim 2 together with a pharmaceutical excipient.

18. A pharmnaceutical composition comprising a compound according to claim 3 together with a pharmaceutical excipient.

19. A pharmaceutical composition comprising a compound according to claim 4 together with a pharmaceutical excipient.

20. A pharmaceutical composition comprising a compound according to claim 5 together with a pharmaceutical excipient.

21. A pharmaceutical composition comprising a compound according to claim 6 together with a pharmaceutical excipient.

22. A pharmaceutical composition comprising a compound according to claim 7 together with a pharmaceutical excipient.

23. A pharmaceutical composition comprising a compound according to claim 10 together with a pharmaceutical excipient.

24. A pharmaceutical composition comprising a compound according to claim 11 together with a pharmaceutical excipient.

25. A pharmaceutical composition comprising a compound according to claim 12 together with a pharmaceutical excipient.

26. A pharmaceutical composition comprising a compound according to claim 13 together with a pharmaceutical excipient.

27. A pharmaceutical composition comprising a compound according to claim 17 together with a pharmaceutical excipient.

28. A method for the treatment of diseases that are improved by $\beta_3$ agonistic activity which comprises administering to a patient in need of such treatment an effective amount of a compound according to claim 1.

29. A method for the treatment of diseases that are improved by $\beta_3$ agonistic activity which comprises administering to a patient in need of such treatment an effective amount of a compound according to claim 2.

30. A method for the treatment of diseases that are improved by $\beta_3$ agonistic activity which comprises administering to a patient in need of such treatment an effective amount of a compound according to claim 3.

31. A method for the treatment of diseases that are improved by $\beta_3$ agonistic activity which comprises administering to a patient in need of such treatment an effective amount of a compound according to claim 4.

32. A method for the treatment of diseases that are improved by $\beta_3$ agonistic activity which comprises administering to a patient in need of such treatment an effective amount of a compound according to claim 5.

33. A method for the treatment of diseases that are improved by $\beta_3$ agonistic activity which comprises administering to a patient in need of such treatment an effective amount of a compound according to claim 6.

34. A method for the treatment of diseases that are improved by $\beta_3$ agonistic activity which comprises administering to a patient in need of such treatment an effective amount of a compound according to claim 7.

35. A method for the treatment of diseases that are improved by $\beta_3$ agonistic activity which comprises administering to a patient in need of such treatment an effective amount of a compound according to claim 10.

36. A method for the treatment of diseases that are improved by $\beta_3$ agonistic activity which comprises administering to a patient in need of such treatment an effective amount of a compound according to claim 11.

37. A method for the treatment of diseases that are improved by $\beta_3$ agonistic activity which comprises administering to a patient in need of such treatment an effective amount of a compound according to claim 12.

38. A method for the treatment of diseases that are improved by $\beta_3$ agonistic activity which comprises administering to a patient in need of such treatment an effective amount of a compound according to claim 13.

39. A method for the treatment of diseases that are improved by $\beta_3$ agonistic activity which comprises administering to a patient in need of such treatment an effective amount of a compound according to claim 14.

* * * * *